US009933206B2

(12) United States Patent
Klett et al.

(10) Patent No.: US 9,933,206 B2
(45) Date of Patent: Apr. 3, 2018

(54) APPARATUS AND METHOD FOR MAINTAINING AN ARTICLE AT A TEMPERATURE THAT IS LESS THAN THE TEMPERATURE OF THE AMBIENT AIR

(71) Applicant: UT-Battelle, LLC, Oak Ridge, TN (US)

(72) Inventors: James Klett, Knoxville, TN (US); Lynn Klett, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 273 days.

(21) Appl. No.: 15/047,939

(22) Filed: Feb. 19, 2016

(65) Prior Publication Data
US 2017/0241702 A1 Aug. 24, 2017

(51) Int. Cl.
*F25D 31/00* (2006.01)
*F25B 23/00* (2006.01)
*F28D 15/04* (2006.01)
*F25B 49/00* (2006.01)
*A61J 1/16* (2006.01)
*A01N 1/02* (2006.01)
*A23L 3/00* (2006.01)
*A47J 41/00* (2006.01)
*F01P 9/06* (2006.01)
*F01P 11/14* (2006.01)

(52) U.S. Cl.
CPC ........... *F25D 31/00* (2013.01); *A01N 1/0252* (2013.01); *A23L 3/00* (2013.01); *A47J 41/00* (2013.01); *A61J 1/165* (2013.01); *F01P 9/06* (2013.01); *F01P 11/14* (2013.01); *F25B 23/006* (2013.01); *F25B 49/005* (2013.01); *F28D 15/046* (2013.01)

(58) Field of Classification Search
CPC .......... F25D 31/00; A61J 1/165; F25B 23/006
See application file for complete search history.

(56) References Cited

U.S. PATENT DOCUMENTS 6,438,964 B1 * 8/2002 Giblin .................. A41D 13/005
62/259.3
6,673,328 B1 1/2004 Klett et al.
(Continued)

OTHER PUBLICATIONS

Klett, James W., "Parametric Investigation of a Graphite Foam Evaporator in a Thermosyphon with Fluorinert and a Silicon CMOS Chip", IEEE Transactions on Device and Materials Reliability, vol. 4, No. 3, Sep. 2004, pp. 626-637.

*Primary Examiner* — Cassey D Bauer
(74) *Attorney, Agent, or Firm* — Colin L. Cini

(57) ABSTRACT

An apparatus for maintaining the temperature of an article at a temperature that is below the ambient air temperature includes an enclosure having an outer wall that defines an interior chamber for holding a volume of sealed air. An insert is disposed inside of the chamber and has a body that is made of a porous graphite foam material. A vacuum pump penetrates the outer wall and fluidly connects the sealed air in the interior chamber with the ambient air outside of the enclosure. The temperatures of the insert and article is maintained at temperatures that are below the ambient air temperature when a volume of a liquid is wicked into the pores of the porous insert and the vacuum pump is activated to reduce the pressure of a volume of sealed air within the interior chamber to a pressure that is below the vapor pressure of the liquid.

20 Claims, 8 Drawing Sheets

(56) References Cited

U.S. PATENT DOCUMENTS

| | | |
|---|---|---|
| 6,763,671 B1 | 7/2004 | Klett et al. |
| 8,215,835 B2 | 7/2012 | Hyde et al. |
| 2002/0189279 A1* | 12/2002 | Pfister .................... F04B 35/00 62/497 |
| 2012/0199330 A1* | 8/2012 | Maurer ................ F25B 39/028 165/168 |

* cited by examiner

| Temperature | | | Pressure [30] | | | | |
|---|---|---|---|---|---|---|---|
| °C | K | °F | Pa | atm | torr(mmHg) | in Hg | psi |
| 0 | 273 | 32 | 611 | 0.00603 | 4.58 | 0.180 | 0.0886 |
| 5 | 278 | 41 | 872 | 0.00861 | 6.54 | 0.257 | 0.1265 |
| 10 | 283 | 50 | 1,228 | 0.01212 | 9.21 | 0.363 | 0.1781 |
| 12 | 285 | 54 | 1,403 | 0.01385 | 10.52 | 0.414 | 0.2034 |
| 14 | 287 | 57 | 1,599 | 0.01578 | 11.99 | 0.472 | 0.2318 |
| 16 | 289 | 61 | 1,817 | 0.01793 | 13.63 | 0.537 | 0.2636 |
| 17 | 290 | 63 | 1,937 | 0.01912 | 14.53 | 0.572 | 0.2810 |
| 18 | 291 | 64 | 2,064 | 0.02037 | 15.48 | 0.609 | 0.2993 |
| 19 | 292 | 66 | 2,197 | 0.02168 | 16.48 | 0.649 | 0.3187 |
| 20 | 293 | 68 | 2,338 | 0.02307 | 17.54 | 0.691 | 0.3392 |

FIG. 7

APPARATUS AND METHOD FOR MAINTAINING AN ARTICLE AT A TEMPERATURE THAT IS LESS THAN THE TEMPERATURE OF THE AMBIENT AIR

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

CROSS-REFERENCE TO RELATED APPLICATIONS

None.

THE NAMES OF THE PARTIES TO A JOINT RESEARCH AGREEMENT

None.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

None.

STATEMENT REGARDING PRIOR DISCLOSURES BY THE INVENTOR OR A JOINT INVENTOR

None.

BACKGROUND OF THE INVENTION

1. Field of the Invention

The present disclosure relates to maintaining articles at reduced temperatures and more particularly to an apparatus and method for maintaining articles at reduced temperatures for extended periods of time without the use of electricity.

2. Description of the Related Art

Historically, ice was harvested from lakes and packed with saw dust inside insulated ice houses for extended periods of time. A block of ice was purchased from an ice house and placed in an individual ice box to maintain meat, dairy, and produce at reduced temperatures in order to delay spoilage. Modern day refrigeration systems use electricity to compress and expand a gas through an expansion valve to achieve similar results. While modern day refrigeration systems are ubiquitous in homes throughout developed regions of the world, electricity distribution and refrigeration systems can be scarce in less-developed regions.

It is known that some vaccines are sensitive to heat and will become less effective or completely ineffective if not kept refrigerated or frozen. The U.S. Department of Health and Human Services, Centers for Disease Control and Prevention suggests refrigerated vaccines be maintained at temperatures between 2° C. and 8° C. (35° F. and 46° F.) and frozen vaccines be maintained at temperatures between −50° C. and −15° C. (−58° F. and 5° F.). The suggested ranges of temperatures are difficult or impossible to maintain for extended periods of time without adequate refrigeration systems and dependable electricity distribution.

What is needed is an apparatus and method for maintaining articles, such as vaccines, transplant organs or food, within their recommended temperature ranges for extended periods of time and without the need for grid-supplied electricity.

BRIEF SUMMARY OF THE INVENTION

Several examples of devices for maintaining articles, such as vaccines, transplant organs or food, at their recommended temperatures for extended periods of time and without the need for grid-supplied electricity are described.

The following summary is provided to facilitate an understanding of some of the innovative features unique to the embodiments and is not intended to be a full description. A full appreciation of the various aspects of the embodiments disclosed can be gained by taking the entire specification, claims, drawings, and abstract as a whole.

According to one example, an apparatus for maintaining the temperature of an article at a temperature that is below the ambient air temperature outside of the apparatus includes an enclosure having an outer wall and a lid that defines an interior chamber for holding a volume of sealed air, and insulates the chamber from the ambient air. An insert is disposed inside of the chamber and has a body that is made of a porous graphite foam material and includes a region for contacting the article. A vacuum pump penetrates the enclosure and fluidly connects the sealed air in the interior chamber with the ambient air outside of the enclosure. The temperatures of the insert and the article are maintained at temperatures that are below the ambient air temperature when a volume of a liquid is wicked into the pores of the porous insert and the vacuum pump is activated to reduce the pressure of the volume of sealed air within the interior chamber to a pressure that is below the vapor pressure of the liquid.

According to another example, a method for maintaining the temperature of an article at a temperature that is less than the temperature of the ambient air includes the steps of: a) providing an apparatus as described immediately above; b) positioning an article inside the enclosure and in contact with the insert at a contacting region; c) wicking a volume of a liquid into at least a portion of the pores of the porous insert; d) sealing the enclosure; and e) activating the vacuum pump to reduce the pressure of the sealed air within the interior chamber to a pressure that is below that of the vapor pressure of the liquid, such that the liquid evaporates, causing the temperatures of the insert and of the article to be maintained at temperatures that are below the ambient air the temperature outside of the enclosure.

BRIEF DESCRIPTION OF THE SEVERAL VIEWS OF THE DRAWING(S)

The apparatus and methods may be better understood with reference to the following drawings and description. Non-limiting and non-exhaustive descriptions are described with reference to the following drawings. The components in the figures are not necessarily to scale, emphasis instead being placed upon illustrating principles. In the figures, like referenced numerals may refer to like parts throughout the different figures unless otherwise specified.

FIG. 7 is an exemplary table listing the vapor pressures of water ($H_2O$) at temperatures between 0° C. and 20° C.

DETAILED DESCRIPTION OF THE INVENTION

Figure 1:
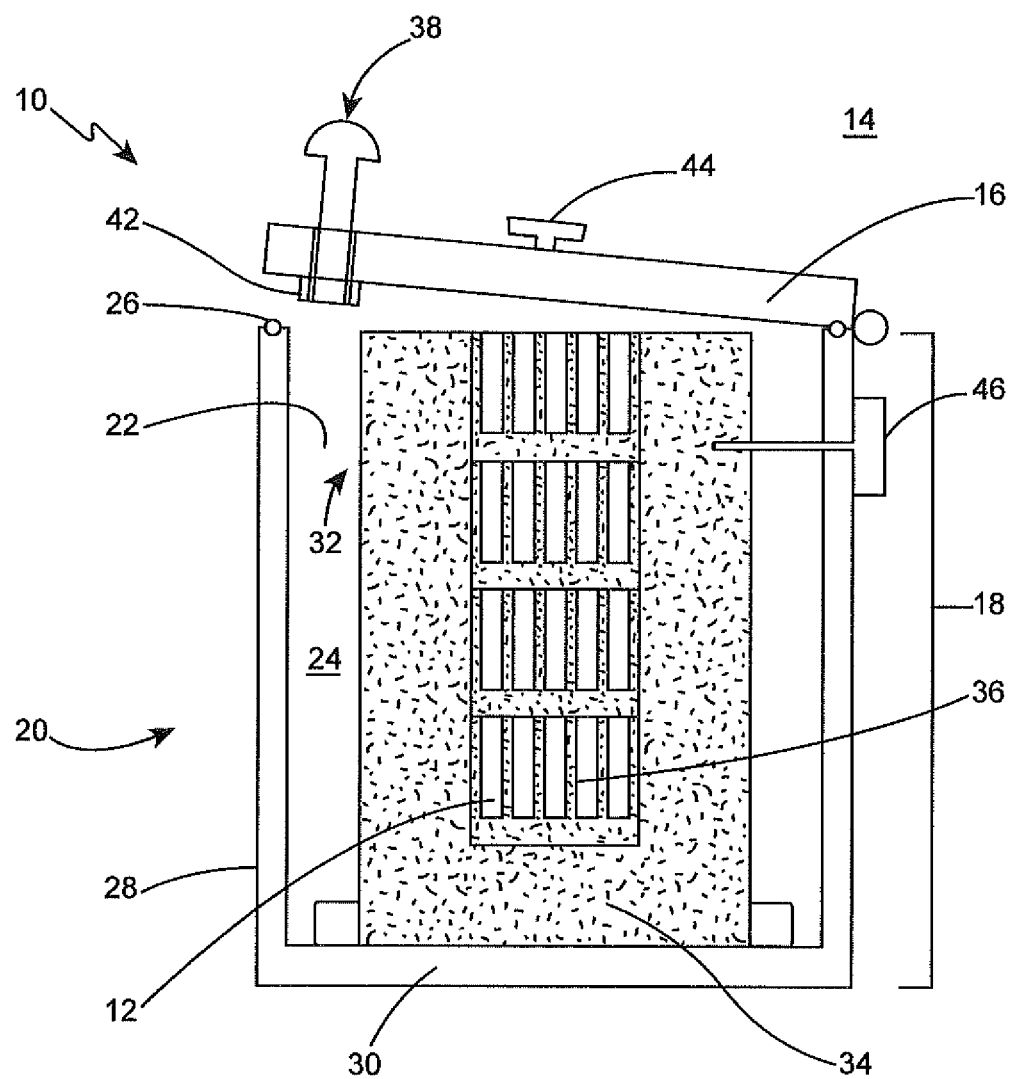
FIG. 1 is a simplified cross sectional view of an exemplary apparatus.
Figure 2:
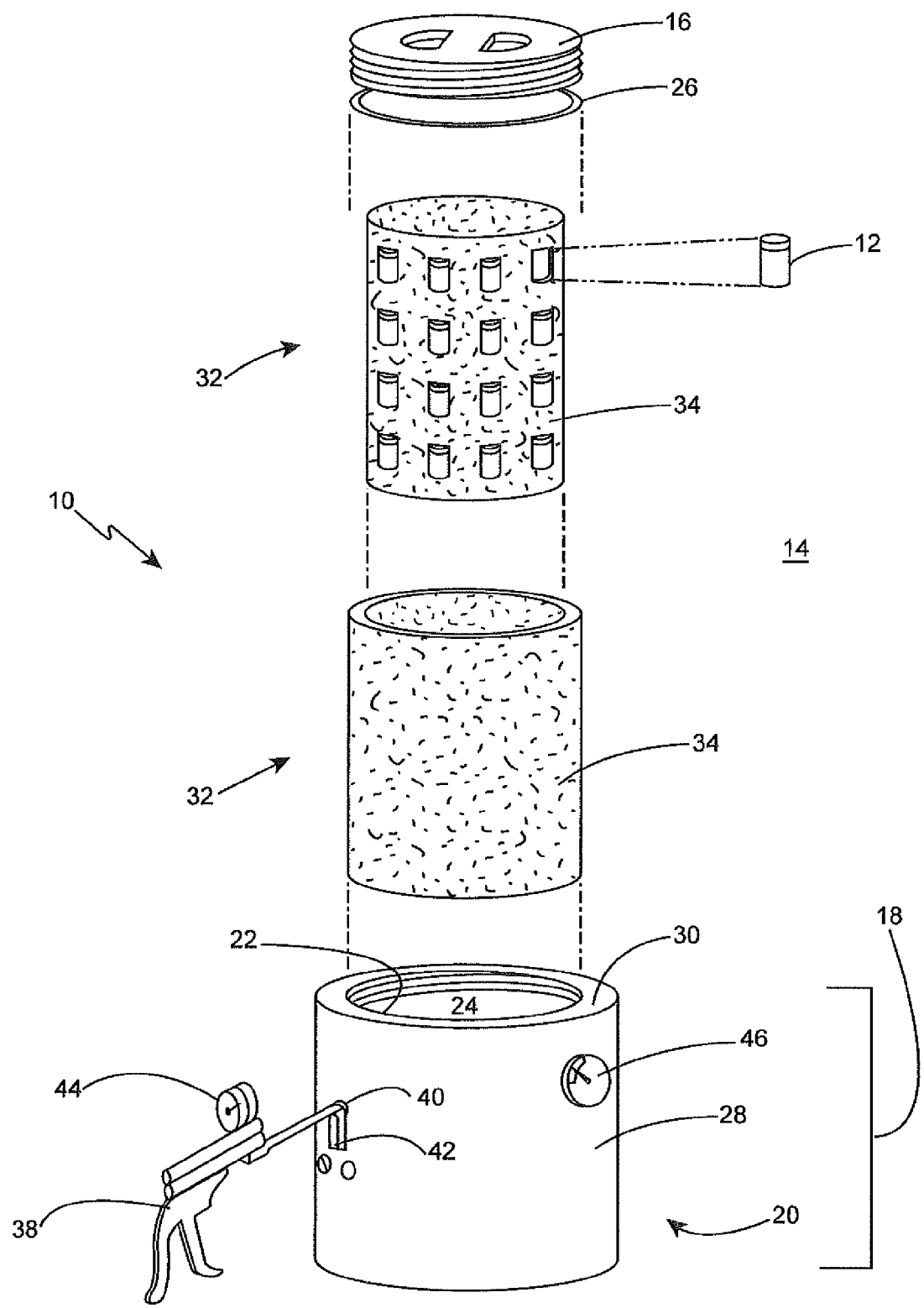
FIG. 2 is an exploded view of another exemplary apparatus.
Figure 3:
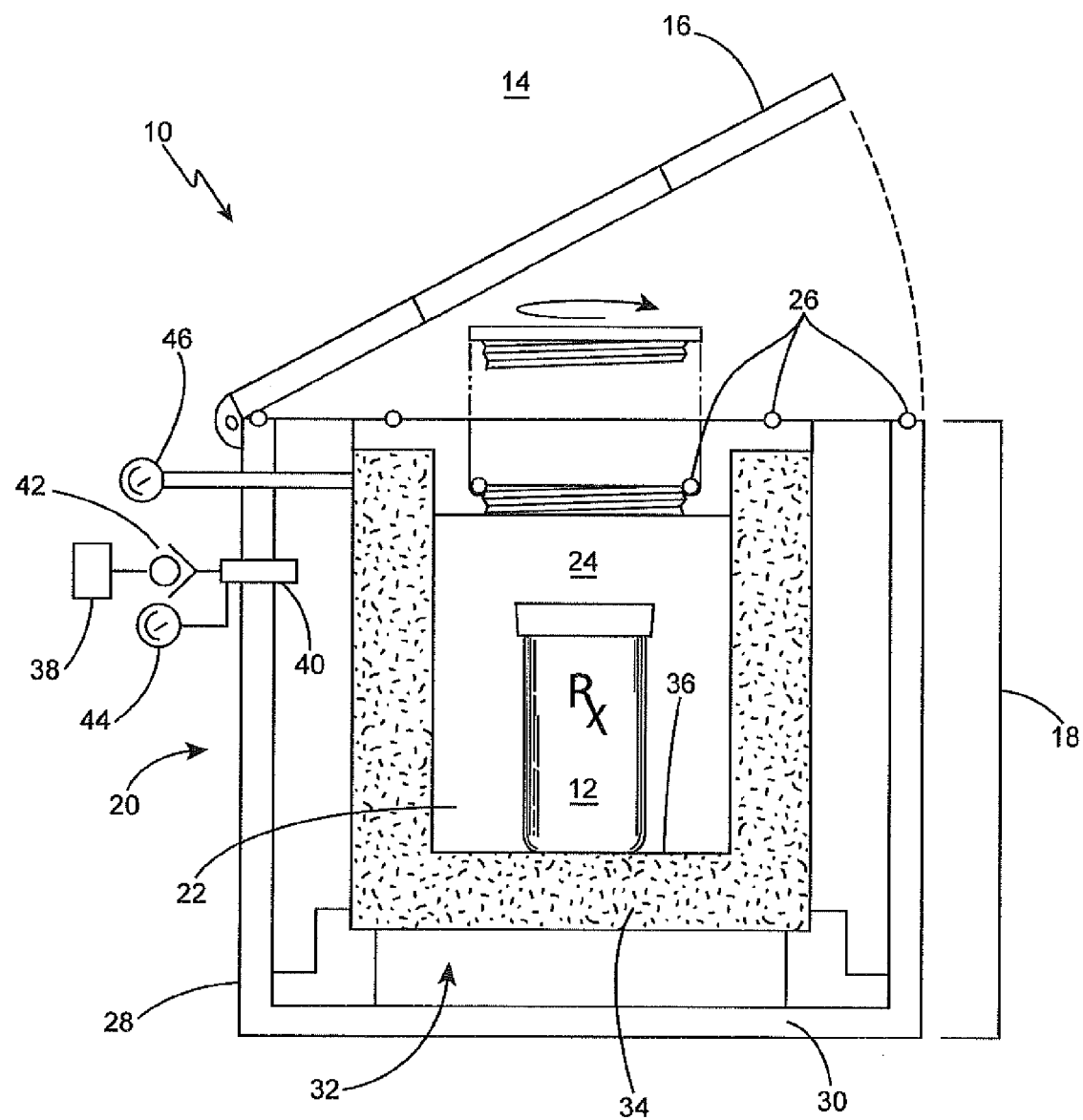
FIG. 3 is a simplified cross sectional view of another exemplary apparatus.
Figure 4:
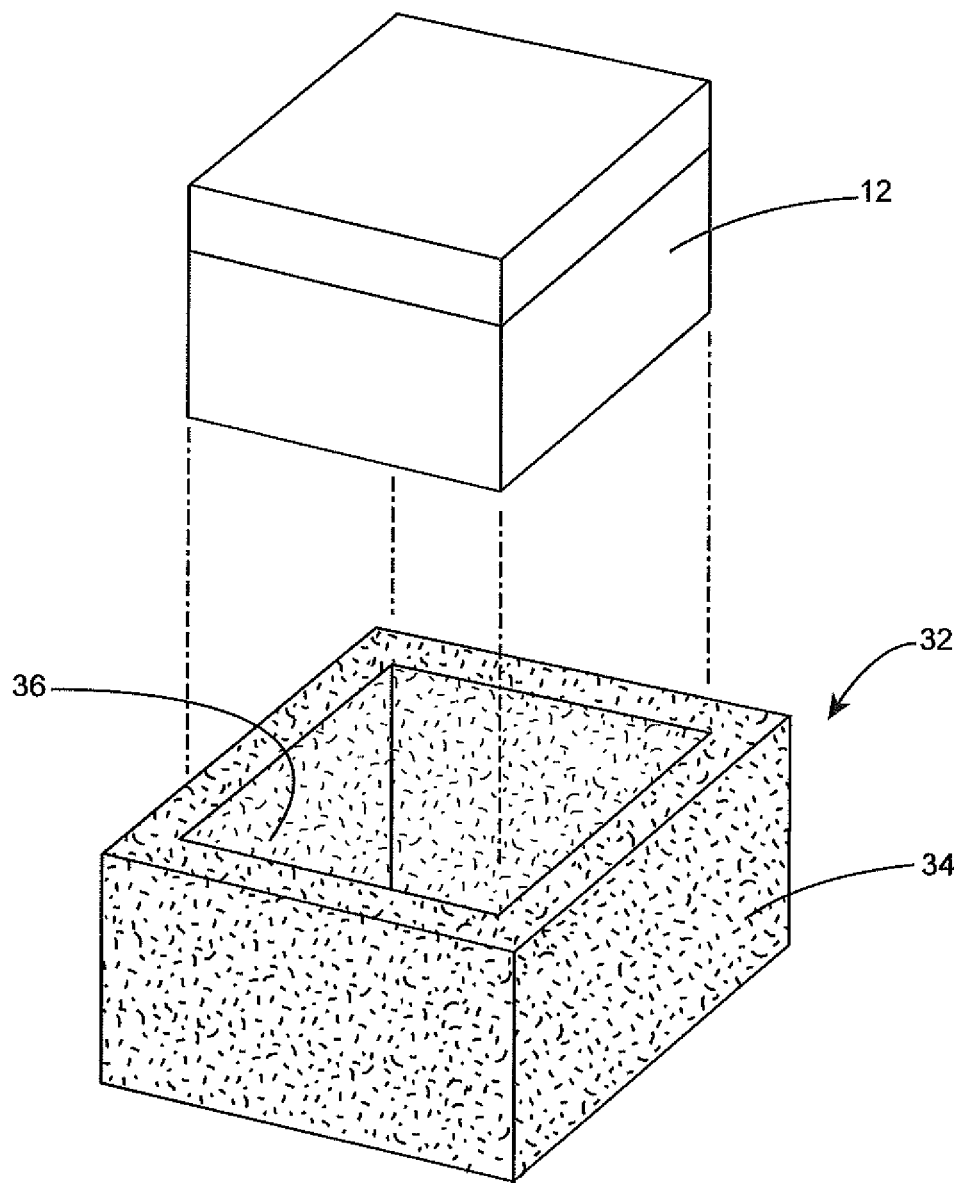
FIG. 4 is an exploded view of an exemplary insert with other features removed for clarity.

With reference first to FIGS. 1-5, various features of an apparatus 10 for maintaining the temperature of an article 12 at a temperature that is below an ambient air 14 temperature are shown. It is to be understood that the ambient air 14 is outside of the apparatus 10. A lid 16 attaches to a body 18 to form an enclosure 20 which defines an interior chamber 22 for storing a volume of sealed air 24. In some examples, the lid 16 is affixed to the body 18 with a hinge, strap, clasp, clamp, latch, elastic lanyard or other attachment device. In other examples, the lid 16 includes threads that engage with complimentary threads on or in the body 18. In other examples, an O-ring or gasket 26 may be disposed between mating surfaces of the lid 16 and the body 18. When assembled together, the lid 16, body 18 and gasket 26 cooperate to form a hermetic seal. Note that in the example of FIG. 3, the hermetic seal may be at least partially maintained when the article 12 is accessed through a separate access port. The enclosure 20 may be cylindrical, square, rectangular or otherwise shaped.

The body 18 includes an outer wall 28 that insulates the interior chamber 22 from the external environment and specifically, the ambient air temperature. The outer wall 28 is preferably made from materials having low thermal conductivity and superior formability such as Polypropylene, Polyethylene, Nylon, Polyester, Polyvinylchloride or other materials having similar properties. Conventional thermoplastic manufacturing processes such as injection molding, blow molding or 3D printing may be used to form the outer wall 28. The outer wall 28 may include a core portion 30 filled with an insulating material such as polyurethane foam and/or engineered ceramic or glass microbeads or microspheres. Microspheres made of soda-lime-borosilicate glass having densities and particle sizes of (0.125 g/cc to 0.60 g/cc) and (65 microns to 16 microns) respectively are available from 3M Energy and Advanced Materials Division for example. In other examples, microspheres can be mixed with polyurethane foam in various ratios to form the core 30.

Figure 5:
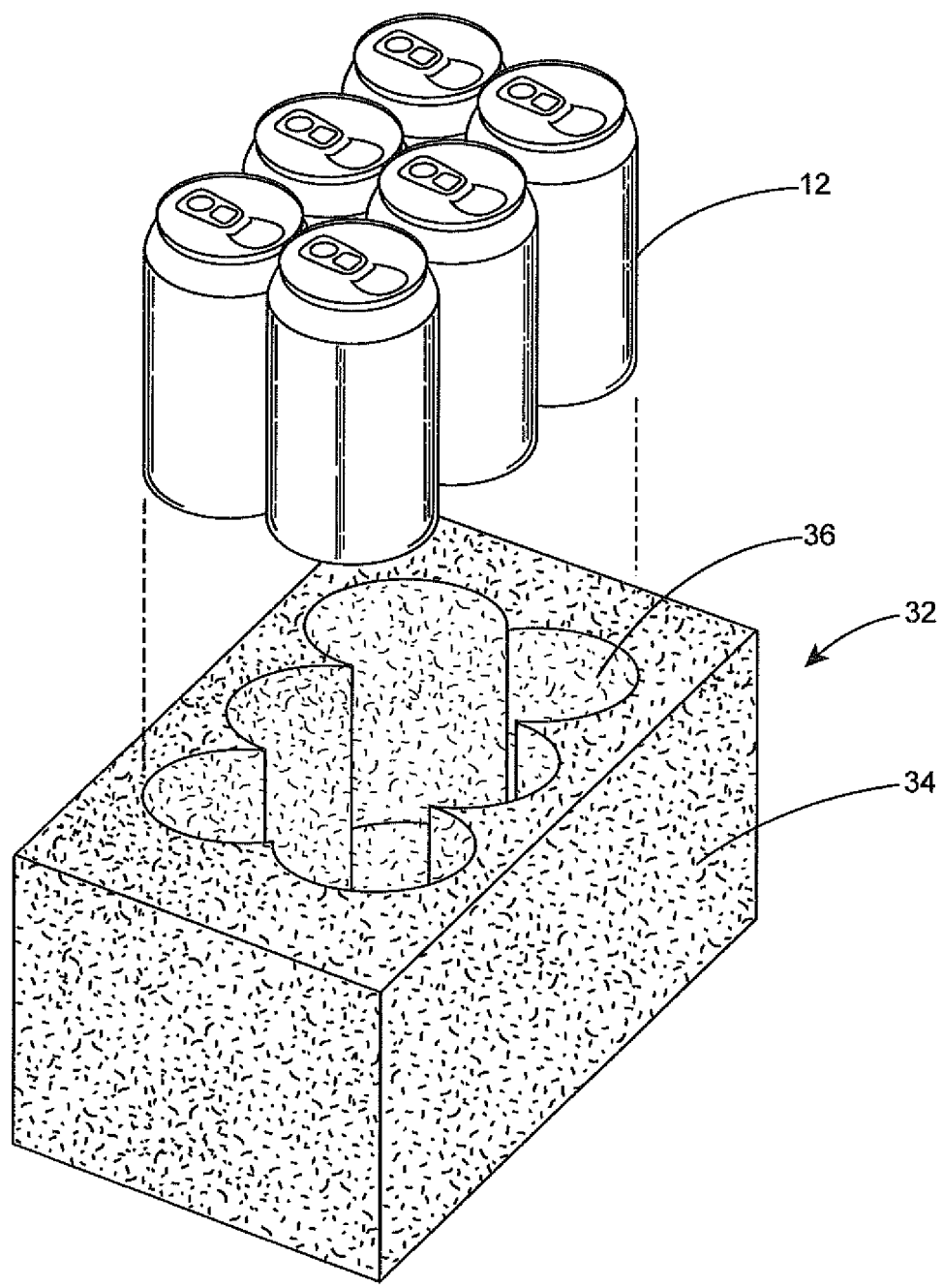
FIG. 5 is an exploded view of another exemplary insert with other features removed for clarity.

Disposed within a portion of the interior chamber 22 is an insert 32 having a body 34 that includes a region 36 for contacting an article 12. Preferably, the region 36 fully contacts (e.g., surrounds), or at least partially contacts the article 12 for increased thermal conduction. In some examples, one or more inserts 32 include regions 36 that are sized and shaped to accommodate specific articles 12 such as vaccine ampules (FIG. 2), transplant organs (FIG. 4) or beverage containers (FIG. 5). In other examples, inserts 32, include contact regions 36 that are shaped specifically for food articles 12 such as fish, meat or poultry.

Figure 6:
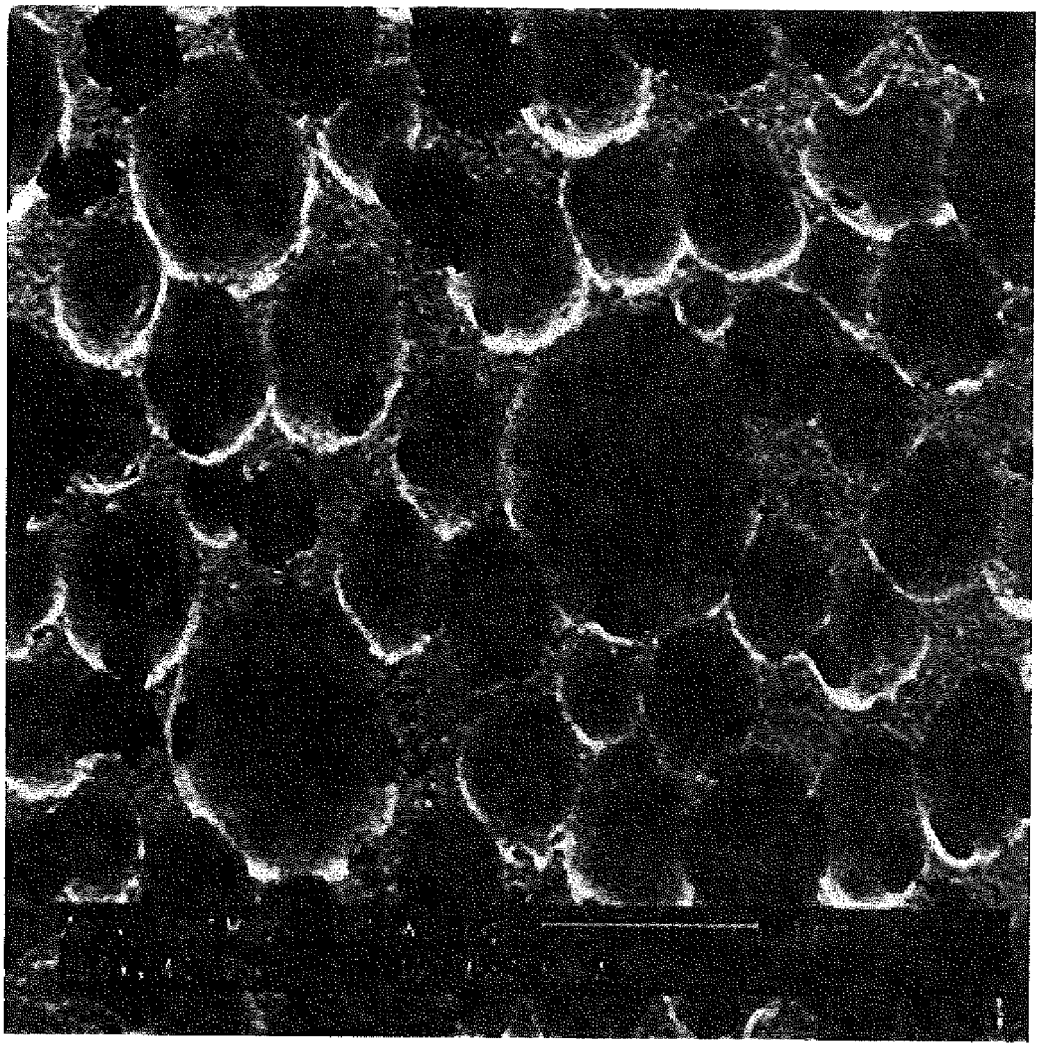
FIG. 6 is a photomicrograph of a porous, graphite foam material of the type used in the exemplary inserts.

The insert 32 is preferably made of a porous, graphite foam material as best illustrated in FIG. 6. Graphite foam is a structure having highly ordered graphitic ligaments, is dimensionally stable, has open porosity, and has excellent thermal management capability. Typical graphite foam materials have densities between approximately 0.38 g/cm³ and 0.93 g/cm³ and thermal conductivities between approximately 50 W/mK and 245 W/mK and can be formed into various sizes and shapes with conventional machine tools. Graphite foam materials are commercially available from Poco Graphite, Inc., 300 Old Greenwood Road, Decatur, Tex. 76234, and Koppers, LLC, 436 Seventh Avenue, Pittsburgh, Pa. 15219-1800.

Additionally, graphite foam articles and methods for manufacturing graphite foams are described in U.S. Pat. No. 6,033,506 "PROCESS FOR MAKING CARBON FOAM"; U.S. Pat. No. 6,037,032 "PITCH-BASED CARBON FOAM HEAT SINK WITH PHASE CHANGE MATERIAL"; U.S. Pat. No. 6,261,485 "PITCH BASED CARBON FOAM AND COMPOSITES"; U.S. Pat. No. 6,287,375 "PITCH BASED FOAM WITH PARTICULATE"; U.S. Pat. No. 6,344,159 "METHOD FOR EXTRUDING PITCH BASED FOAM"; U.S. Pat. No. 6,387,343 "PITCH-BASED CARBON FOAM AND COMPOSITES"; U.S. Pat. No. 6,398,994 "METHOD OF CASTING PITCH BASED FOAM"; U.S. Pat. No. 6,399,149 "PITCH-BASED CARBON FOAM HEAT SINK WITH PHASE CHANGE MATERIAL"; U.S. Pat. No. 6,491,891 "GELCASTING POLYMERIC PRECURSORS FOR PRODUCING NET-SHAPED GRAPHITES"; U.S. Pat. No. 6,656,443 "PITCH BASED CARBON FOAM AND COMPOSITES"; U.S. Pat. No. 6,673,328 "PITCH BASED CARBON FOAM AND COMPOSITES AND USES THEREOF"; U.S. Pat. No. 6,780,505 "PITCH-BASED CARBON FOAM HEAT SINK WITH PHASE CHANGE MATERIAL"; U.S. Pat. No. 6,855,744 "GELCASTING POLYMERIC PRECURSORS FOR PRODUCING NET-SHAPED GRAPHITES"; U.S. Pat. No. 7,070,755 "PITCH-BASED CARBON FOAM AND COMPOSITES AND USE THEREOF"; U.S. Pat. No. 7,456,131 "INCREASED THERMAL CONDUCTIVITY MONOLITHIC ZEOLITE STRUCTURES"; and U.S. Pat. No. 7,670,682 "METHOD AND APPARATUS FOR PRODUCING A CARBON BASED FOAM ARTICLE HAVING A DESIRED THERMAL-CONDUCTIVITY GRADIENT", which are each herein incorporated by reference as if included at length.

A vacuum pump 38 penetrates through the enclosure 20 and fluidly connects the sealed air 24 in the interior chamber 22 with the ambient air 14 outside of the enclosure 20. The vacuum pump 38 includes a one-way check valve and evacuates the sealed air 24 to the ambient air 14, which lowers the pressure of the sealed air 24. The vacuum pump 38 may be electrically powered, air powered, or preferably, manually powered by a human. In one example, a manual vacuum pump 38 of the type distributed under the trade name MITYVAC from Lincoln Industrial Corporation attaches, via a length of hose, to a barbed fitting 40 (FIG. 2) that penetrates the enclosure 20. A valve 42 between the interior chamber 22 and the vacuum pump 38 can be closed to maintain the reduced pressure of the sealed air 24. The valve 42 may subsequently be opened to normalize the pressure between the sealed air 24 and the ambient air 14 prior to opening the lid 16. A vacuum pressure gauge 44 may be used to indicate the pressure of the sealed air 24 and to monitor for gasket 26 leakage.

A temperature gauge 46 may also penetrate the enclosure 20 for monitoring the temperature of the insert 32 and the article 12. A sensing element or probe contacts the insert 32 and an indicating element or dial is disposed and viewable outside of the enclosure 20. In some examples, the temperature gauge 46 is a thermometer using liquid expansion as an indication of temperature. In other examples, the temperature gauge 46 is a thermocouple that uses measured voltage as an indication of temperature. In one example, a battery or photovoltaic cell provides the necessary voltage to power the thermocouple and its display. In another example, the pumping action of the vacuum pump 38 or a separate crank charges a capacitor or rechargeable battery to power the thermocouple and display. In other examples, a temperature data memory and alarm are connected to the thermocouple circuit to provide temperature audit and alert capabilities. All penetrations through the enclosure 20 are hermetically sealed with a gasket and/or a sealant.

The vapor pressure of a liquid is defined as the equilibrium pressure of a vapor above the liquid level in a sealed space. When equilibrium is reached, the number of molecules of liquid evaporating equals the number of vapor molecules condensing. By reducing the pressure inside the sealed space, the molecules of liquid have a greater tendency to evaporate to form water vapor. Under a vacuum, liquids boil at a much lower temperature than at atmospheric pressure. Without increasing the temperature, energy for boiling comes from the liquid itself and, consequently, the temperature of the liquid is reduced and the liquid freezes. FIG. 7 shows a table listing the vapor pressure of water at temperatures between 0° C. and 20° C.

When water is added to the interior chamber 22 it will wick into the pores of the graphite foam insert 32. When the pressure of the sealed air 24 is reduced to approximately 4.58 torr (mmHg) with the vacuum pump 38, the water will cool and eventually freeze. The temperature of the insert 32 will approach 0° C. and will maintain the temperature of an article 12 at a temperature that is below the ambient air 14 temperature outside of the enclosure 20. This example assumes that the ambient air temperature is above 0° C. Since the recommended storage temperatures of most vaccines are between approximately 2° C. and 8° C., the pressure of the sealed air 24 can be maintained with the vacuum pump 38 between 5.2 torr (mmHg) and 8.0 torr (mmHg). In order to maintain a beverage container at approximately 5° C., the pressure of the sealed air 24 can be maintained with the vacuum pump 38 at approximately 6.54 torr (mmHg). In some examples, the volume of liquid added is up to 50% of the pore volume of the graphite foam insert. In other examples, the volume of liquid added is up to 75% of the pore volume of the graphite foam insert. In other example, the volume of liquid added is up to 100% of the pore volume of the graphite foam insert. In other examples, the volume of liquid added is greater than 100% of the pore volume of the graphite foam insert. While the previous examples discuss water as the liquid, other liquids would work similarly and are also contemplated. Nontoxic and nonflammable liquids are preferred.

Figure 8:
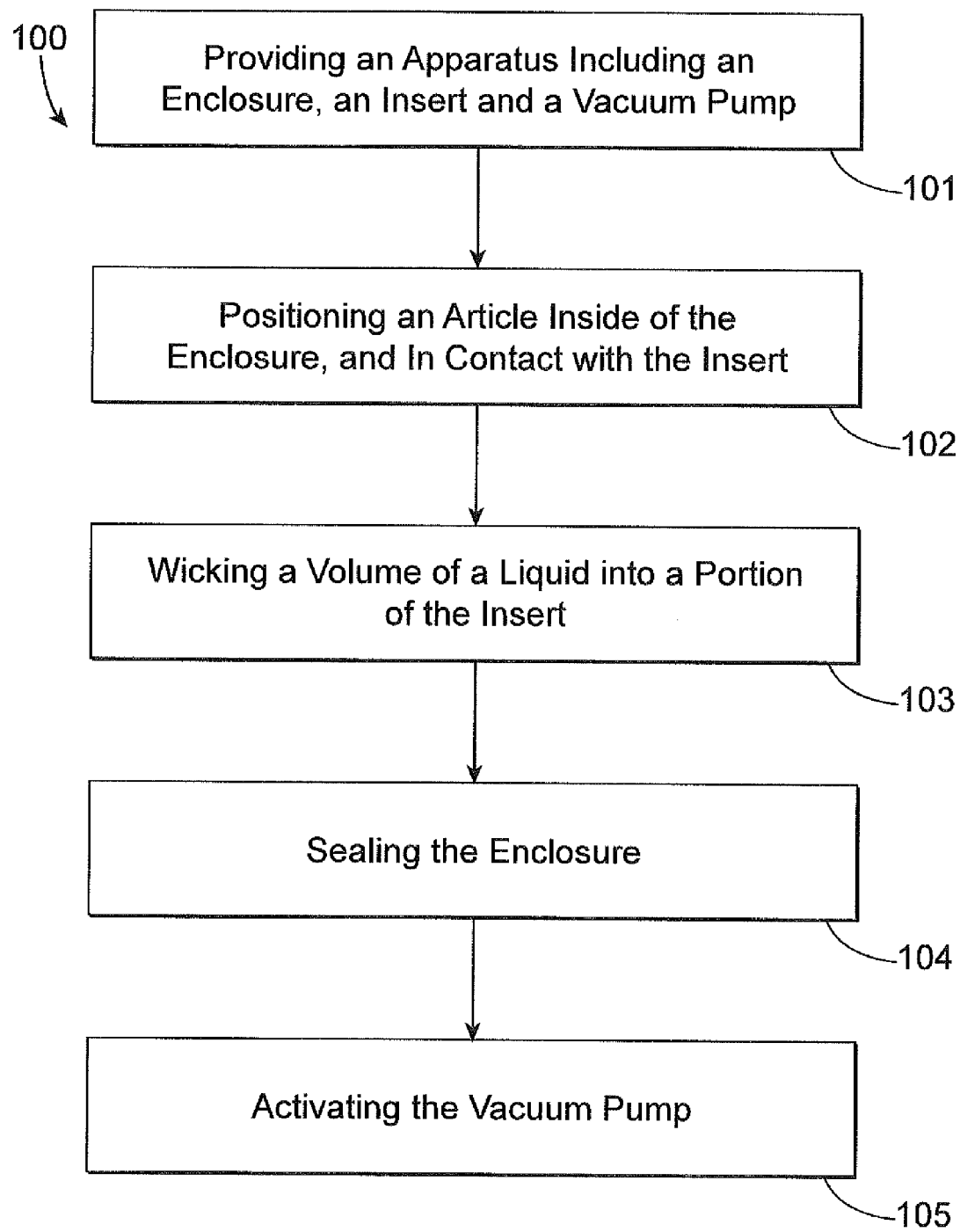
FIG. 8 is a schematic representation of a series of exemplary method steps.

FIG. 8 schematically illustrates a method 100 for maintaining an article at a temperature that is below the ambient air temperature. In a first step represented by block 101, an enclosure 20, an insert 32 and a vacuum pump 38 are provided. In a second step represented by block 102, an article 12 is positioned against the insert 32 at a contacting region 36. In a third step represented by block 103, a volume of a liquid is wicked into the graphite foam insert 32. In a forth step represented by block 104, the enclosure is hermetically sealed. And, in a final step represented by block 105, the vacuum pump is activated to reduce the pressure of the sealed air to a pressure that is below the vapor pressure of the liquid.

While this disclosure describes and enables several examples of an apparatus and a method for maintaining an article at a temperature that is below the ambient air temperature, other examples and applications are contemplated. Accordingly, the invention is intended to embrace those alternatives, modifications, equivalents, and variations as fall within the broad scope of the appended claims. The technology disclosed and claimed herein may be available for licensing in specific fields of use by the assignee of record.

What is claimed is:

1. An apparatus for maintaining the temperature of an article at a temperature that is less than the temperature of the ambient air outside of the apparatus comprising:
   an enclosure having an outer wall and a lid that define an interior chamber for holding a volume of sealed air, said enclosure insulates the interior chamber from the ambient air that is outside said enclosure;
   an insert disposed inside of the interior chamber, said insert having a body that is made of a porous graphite foam material and having a region for contacting the article;
   a vacuum pump penetrating through the enclosure, said vacuum pump fluidly connecting the sealed air in the interior chamber with the ambient air outside of said enclosure; and
   wherein the temperatures of said insert and of the article are maintained at temperatures that are below the ambient air temperature when a volume of liquid is wicked into the pores of the porous graphite foam insert and said vacuum pump is activated to reduce the pressure of the sealed air within the interior chamber to a pressure that is below the vapor pressure of the liquid.

2. The apparatus of claim 1 wherein said outer wall comprises ceramic microspheres.

3. The apparatus of claim 1 wherein said enclosure comprises a body and a lid and, together with a gasket, the body, the lid and the gasket create a hermetic seal when assembled together.

4. The apparatus of claim 1 wherein said vacuum pump is a manually operated vacuum pump.

5. The apparatus of claim 1 and further comprising a temperature gauge penetrating the enclosure and having a sensing element for contacting said insert and an indicating element for displaying the temperature of said insert at a position that is viewable outside of said enclosure.

6. The apparatus of claim 1 and further comprising a vacuum pressure gauge penetrating the enclosure for monitoring and displaying the pressure of the sealed air in the interior chamber.

7. The apparatus of claim 1 wherein, when the vacuum pump is activated, the sealed air pressure within the interior chamber is maintained at between approximately 5.2 torr (mmHg) and 8.0 torr (mmHg).

8. The apparatus of claim 1 wherein when a volume of liquid is wicked into the pores of the porous insert, the liquid is water.

9. A method for maintaining the temperature of an article at a temperature that is less than the temperature of the ambient air comprising the steps of:
   a) providing an enclosure having an outer wall and a lid that define an interior chamber containing a volume of sealed air, said enclosure insulates the chamber from the ambient air, an insert disposed inside the chamber, said insert having a body that is made of a porous graphite foam material and including a region for contacting the article, and a vacuum pump penetrating the enclosure, said vacuum pump fluidly connecting the sealed air within the interior chamber with the ambient air outside of said enclosure;
b) positioning an article inside said enclosure and in contact with said insert at a contacting region;
c) wicking a volume of a liquid into at least a portion of the pores of the porous insert;
d) sealing said enclosure; and
e) activating said vacuum pump to reduce the pressure of the sealed air within the interior chamber to a pressure that is below that of the vapor pressure of the liquid, such that the liquid evaporates, causing the temperatures of said insert and of the article to be maintained at temperatures that are below the ambient air the temperature outside of the enclosure.

10. The method of claim 9 wherein the providing step a) includes an outer wall comprising ceramic microspheres.

11. The method of claim 9 wherein the sealing step d) includes assembling a lid and a gasket to a body of said enclosure to create a hermetic seal.

12. The method of claim 9 wherein the activating step e) includes manually pumping said vacuum pump.

13. The apparatus of claim 9 wherein the activating step e) includes maintaining the sealed air pressure within the interior chamber at a pressure that is between approximately 5.2 torr (mmHg) and 8.0 torr (mmHg) with said vacuum pump.

14. The method of claim 9 and further comprising the step of:
f) monitoring the temperature of said insert with a temperature gauge penetrating through said enclosure and having a sensing element for contacting said insert and an indicating element for displaying the temperature of said insert outside of said enclosure.

15. The method of claim 9 wherein the activating step e) further includes monitoring a vacuum pressure with a vacuum pressure gauge penetrating through said enclosure that is indicative of the vacuum pressure of the sealed air in the interior chamber.

16. The apparatus of claim 9 wherein the wicking step c) includes wicking a volume of water into the pores of the porous insert.

17. A human-powered refrigeration system comprising:
a hermetically sealed enclosure defining an interior chamber for holding a volume of sealed air;
an insert made of porous graphite foam disposed in the interior chamber;
a volume of a liquid wicked inside said porous graphite foam insert;
a manual vacuum pump for reducing the pressure of the sealed air within the interior chamber; and
wherein the temperature of the insert is maintained at a temperature that is less than the temperature of the ambient air outside of the enclosure when a human activates the manual vacuum pump to reduce the pressure of the volume of sealed air within the interior chamber to a pressure that is below the vapor pressure of the liquid.

18. The system of claim 17 wherein the liquid is water.

19. The system of claim 17 wherein the sealed air pressure within the interior chamber is maintained at a pressure that is between approximately 5.2 torr (mmHg) and 8.0 torr (mmHg) with said vacuum pump.

20. The apparatus of claim 17 wherein said enclosure includes and outer wall that comprises ceramic microspheres.

* * * * *